United States Patent
Coulthard et al.

(10) Patent No.: US 10,561,534 B2
(45) Date of Patent: Feb. 18, 2020

(54) DRESSING WITH FLUID ACQUISITION AND DISTRIBUTION CHARACTERISTICS

(71) Applicant: KCI Licensing, Inc., San Antonio, TX (US)

(72) Inventors: Richard Daniel John Coulthard, Verwood (GB); Timothy Mark Robinson, Shillingstone (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 525 days.

(21) Appl. No.: 15/314,426

(22) PCT Filed: Jun. 4, 2015

(86) PCT No.: PCT/US2015/034289
§ 371 (c)(1),
(2) Date: Nov. 28, 2016

(87) PCT Pub. No.: WO2015/188003
PCT Pub. Date: Dec. 10, 2015

(65) Prior Publication Data
US 2017/0128269 A1    May 11, 2017

Related U.S. Application Data

(60) Provisional application No. 62/008,395, filed on Jun. 5, 2014.

(51) Int. Cl.
*A61F 13/02* (2006.01)
*A61F 13/00* (2006.01)
*A61M 1/00* (2006.01)

(52) U.S. Cl.
CPC .. *A61F 13/00068* (2013.01); *A61F 13/00029* (2013.01); *A61F 13/00034* (2013.01);
(Continued)

(58) Field of Classification Search
CPC .......... A61F 13/00029; A61F 13/00034; A61F 13/00068; A61F 13/022; A61F 2013/00217
(Continued)

(56) References Cited

U.S. PATENT DOCUMENTS 1,355,846 A   10/1920   Rannells
1,944,834 A    1/1934   Bennett
(Continued)

FOREIGN PATENT DOCUMENTS

AU    550575 B2    3/1986
AU    745271 B2    3/2002
(Continued)

OTHER PUBLICATIONS

Office Action for related U.S. Appl. No. 14/965,675, dated Dec. 12, 2018.
(Continued)

*Primary Examiner* — Susan S Su

(57) ABSTRACT

Systems, methods, and apparatuses for treating a tissue site are described. In some embodiments, the system may include a pouch having an upstream layer, a downstream layer, and an absorbent member enclosed between the upstream layer and the downstream layer. The upstream layer and the downstream layer may each include a hydrophobic side and a hydrophilic side. The hydrophilic side of both the upstream layer and the downstream layer may be positioned facing the absorbent member. The hydrophobic side of both the upstream layer and the downstream layer may form a portion of an exterior surface of the pouch such that fluid incident on the pouch is distributed laterally along the exterior surface of the pouch before being absorbed by the absorbent member.

14 Claims, 4 Drawing Sheets

(52) U.S. Cl.
CPC ...... *A61F 13/00063* (2013.01); *A61F 13/022* (2013.01); *A61M 1/0088* (2013.01); *A61F 2013/00217* (2013.01)

(58) Field of Classification Search
USPC ................................................ 604/304–308
See application file for complete search history.

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,617,021 A * | 10/1986 | Leuprecht ......... A61F 13/00029 493/340 |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |

(56) References Cited

U.S. PATENT DOCUMENTS

| | | |
|---|---|---|
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A * | 11/1998 | George ............ A61F 13/15252 |
| | | 604/364 |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 | 3/2001 | Wulff et al. |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 * | 12/2014 | Mathies ............ A61F 13/00012 |
| | | 424/443 |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082925 A1 * | 4/2004 | Patel ................ A61L 15/44 |
| | | 604/289 |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 * | 1/2006 | Langen ............ A61F 13/00008 |
| | | 428/447 |
| 2006/0020235 A1 * | 1/2006 | Siniaguine ........ A61F 13/00995 |
| | | 602/41 |
| 2006/0079852 A1 | 4/2006 | Bubb et al. |
| 2006/0083776 A1 | 4/2006 | Bott et al. |
| 2006/0154546 A1 | 7/2006 | Murphy et al. |

(56) References Cited

U.S. PATENT DOCUMENTS

| | | |
|---|---|---|
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0009812 A1* | 1/2008 | Riesinger .......... A61F 13/00012 604/305 |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1* | 8/2009 | Eckstein ........... A61F 13/00063 602/43 |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1* | 9/2009 | Vitaris .............. A61F 13/00063 604/304 |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1* | 2/2010 | Keller ............... A61F 13/00017 604/360 |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1* | 10/2010 | Lu .................... A61L 15/26 602/44 |
| 2010/0286582 A1* | 11/2010 | Simpson ............ A61F 13/022 602/43 |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1* | 8/2011 | Dubrow ............. A61F 13/02 602/54 |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257612 A1* | 10/2011 | Locke ................ A61F 13/02 604/319 |
| 2011/0257617 A1 | 10/2011 | Franklin |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1* | 2/2012 | Dehn ................. A61F 13/00008 34/282 |
| 2012/0040131 A1 | 2/2012 | Speer |
| 2012/0059339 A1* | 3/2012 | Gundersen ............ A45D 34/04 604/304 |
| 2012/0123359 A1 | 5/2012 | Reed |
| 2012/0143157 A1 | 6/2012 | Riesinger |
| 2012/0258271 A1 | 10/2012 | Maughan |
| 2012/0310186 A1* | 12/2012 | Moghe .................. A61L 15/26 604/304 |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0150763 A1* | 6/2013 | Mirzaei .............. A61L 15/225 602/43 |
| 2013/0152945 A1 | 6/2013 | Locke et al. |
| 2013/0172843 A1* | 7/2013 | Kurata ................ A61F 13/022 604/372 |
| 2013/0189339 A1 | 7/2013 | Vachon |
| 2013/0261585 A1* | 10/2013 | Lee .................... A61F 13/8405 604/385.01 |
| 2014/0039423 A1 | 2/2014 | Riesinger |
| 2014/0039424 A1 | 2/2014 | Locke |
| 2014/0058309 A1* | 2/2014 | Addison ............ A61F 13/0203 602/44 |
| 2014/0107561 A1* | 4/2014 | Dorian ................ A61M 35/00 604/23 |
| 2014/0107562 A1* | 4/2014 | Dorian ................ A61M 35/00 604/24 |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1* | 6/2014 | Patel .................... A61L 15/44 427/2.31 |
| 2014/0309574 A1 | 10/2014 | Cotton |
| 2014/0336557 A1* | 11/2014 | Durdag ................ A61L 15/26 602/48 |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0057625 A1 | 2/2015 | Coulthard |
| 2015/0080788 A1 | 3/2015 | Blott et al. |
| 2015/0080815 A1* | 3/2015 | Chakravarthy ......... A61L 15/44 604/304 |
| 2015/0119830 A1 | 4/2015 | Luckemeyer et al. |
| 2015/0119833 A1 | 4/2015 | Coulthard et al. |
| 2015/0141941 A1 | 5/2015 | Allen et al. |
| 2015/0190286 A1 | 7/2015 | Allen et al. |
| 2015/0290041 A1* | 10/2015 | Richard ............ A61F 13/00029 604/372 |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A | 7/1988 |
| EP | 0358302 A2 | 3/1990 |
| EP | 0538917 A1 | 4/1993 |
| EP | 0630629 A1 | 12/1994 |

(56) References Cited

FOREIGN PATENT DOCUMENTS

| | | |
|---|---|---|
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2005205120 A | 8/2005 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
Japanese office action for corresponding application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related appplication PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Office Action for related U.S. Appl. No. 14/965,675, dated Aug. 9, 2018.
Office Action for related U.S. Appl. No. 15/307,472, dated Oct. 18, 2018.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.

(56) References Cited

OTHER PUBLICATIONS

International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion date dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
NDP 1000 Negative Pressure Wound Terapy System, Kalypto Medical, pp. 1-4.
Partial International Search Report date dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
Partial International Search Report dated Jul. 31, 2009 for PCT International Application No. PCT/US2009/036217.
International Search Report and Written Opinion dated Oct. 19, 2010; PCT International Application No. PCT/US2009/036217.
International Search Report and Written Opinion dated Jan. 5, 2010; PCT International Application No. PCT/US2009/057130.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
Extended European Search Report for related application 17177013.4, dated Mar. 19, 2018.
Extended European Search Report for related application 16793298.7, dated Mar. 27, 2018.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
NPD 1000 Negative Pressure Would Therapy System, Kalypto Medical, pp. 1-4, dated Sep. 2008.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
Office Action for related U.S. Appl. No. 15/600,451, dated Nov. 27, 2019.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

(56) References Cited

OTHER PUBLICATIONS

Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

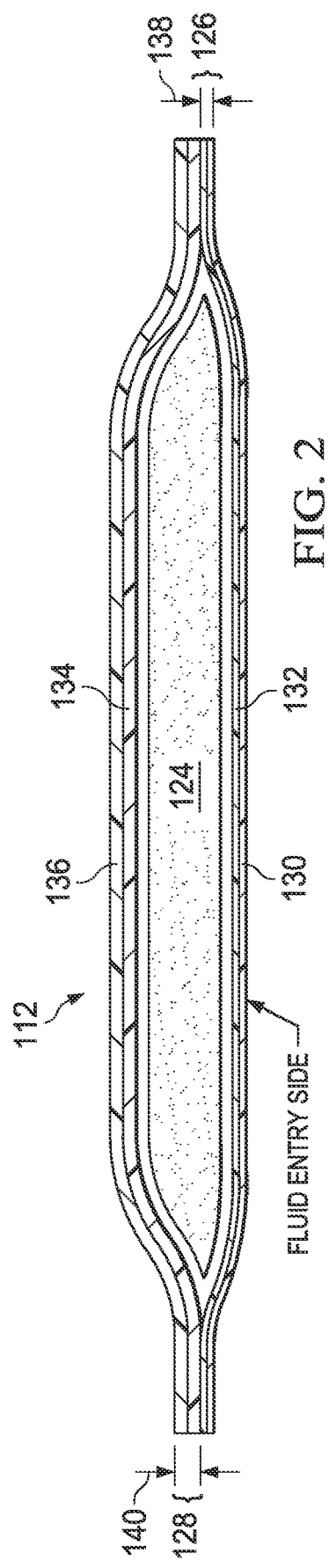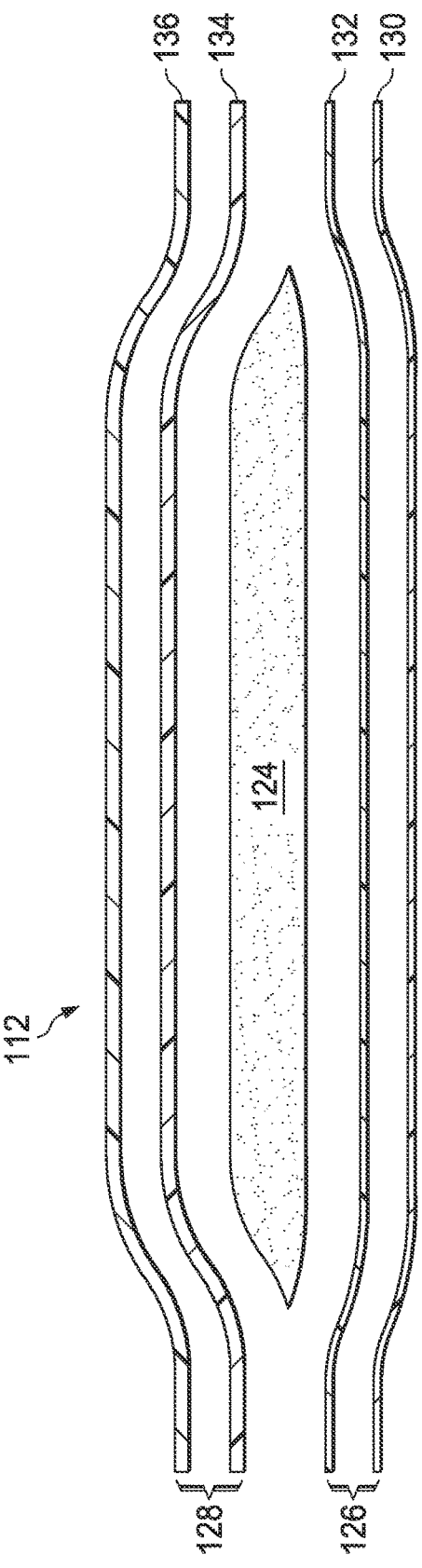

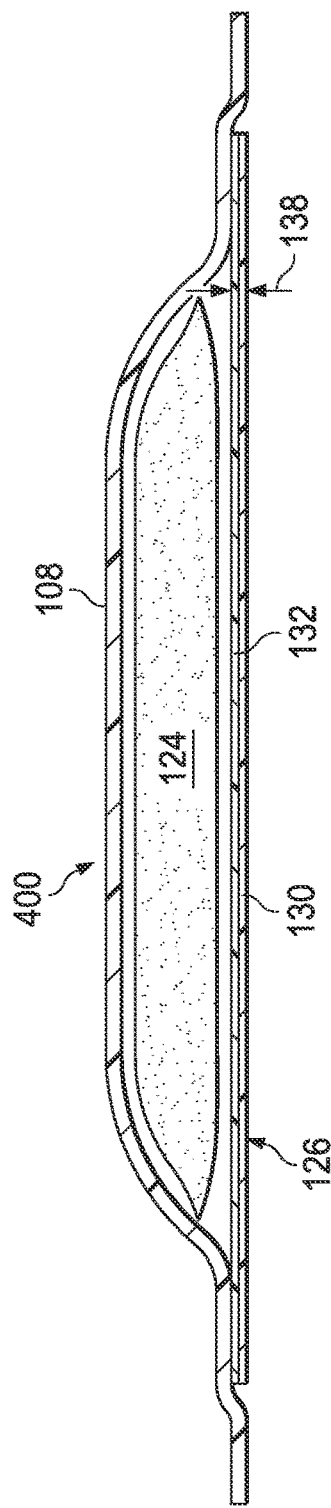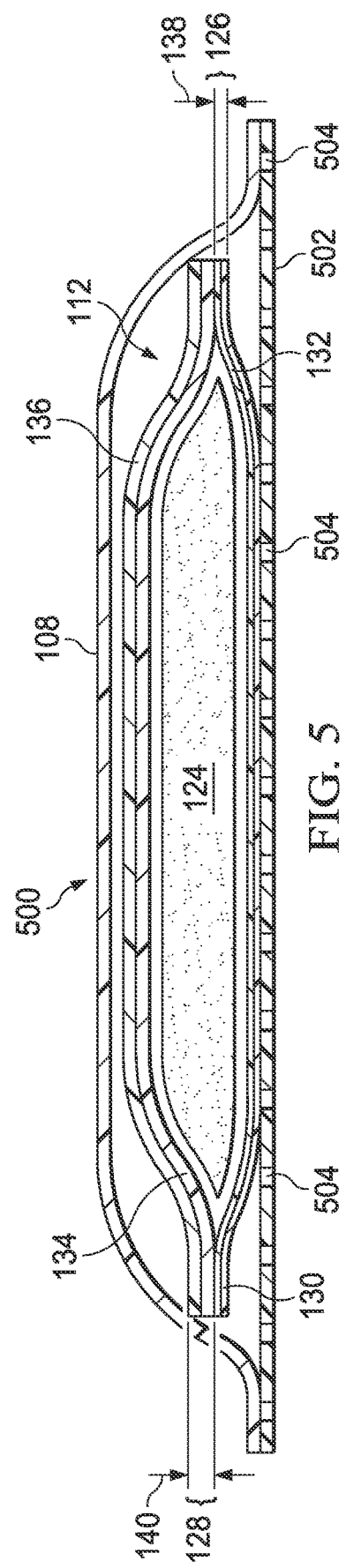

DRESSING WITH FLUID ACQUISITION AND DISTRIBUTION CHARACTERISTICS

RELATED APPLICATIONS

This application claims the benefit, under 35 USC § 119(e), of the filing of U.S. Provisional Patent Application Ser. No. 62/008,395, entitled "Dressing With Fluid Acquisition And Distribution Characteristics," filed Jun. 5, 2014, which is incorporated herein by reference for all purposes.

TECHNICAL FIELD

This disclosure relates generally to medical treatment systems for treating tissue sites and processing fluids. More particularly, but not by way of limitation, the disclosure relates to a dressing capable of laterally and vertically distributing fluids in the dressing. The dressing may be used with or without reduced pressure to treat a tissue site.

BACKGROUND

Clinical studies and practice have shown that reducing pressure in proximity to a tissue site can augment and accelerate growth of new tissue at the tissue site. The applications of this phenomenon are numerous, but have proven particularly advantageous for treating wounds. Regardless of the etiology of a wound, whether trauma, surgery, or another cause, proper care of the wound is important to the outcome. Treatment of wounds with reduced pressure may be commonly referred to as "reduced-pressure wound therapy," but is also known by other names, including "negative-pressure therapy," "negative pressure wound therapy," and "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor. The development and operation of reduced-pressure systems, components, and processes continues to present significant challenges to manufacturers, healthcare providers, and patients. In particular, reduced-pressure dressings that include an absorbent member positioned proximate to a tissue site may experience absorbent material loss or inefficient absorption that negatively impacts the ability of a reduced-pressure system to provide reduced-pressure therapy to a tissue site.

SUMMARY

According to an illustrative embodiment, a system for treating a tissue site may include a manifold, a sealing member, a pouch, and a reduced-pressure source. The manifold may be adapted to be placed adjacent to the tissue site. The sealing member may be adapted to cover the tissue site and the manifold to provide a fluid seal at the tissue site. The pouch may be for positioning between the manifold and the sealing member. The pouch may include an upstream layer having a hydrophilic side and a hydrophobic side, and a downstream layer having a hydrophilic side and a hydrophobic side. The pouch may also include an absorbent member enclosed between the upstream layer and the downstream layer. The hydrophilic side of the upstream layer may be positioned facing the absorbent member, and the hydrophilic side of the downstream layer may be positioned facing the absorbent member. The reduced-pressure source may be in fluid communication with the manifold through the sealing member.

According to another illustrative embodiment, an apparatus for collecting fluid from a tissue site may include an upstream layer, a downstream layer, and an absorbent member. The upstream layer may have a hydrophilic side and a hydrophobic side, and the downstream layer may have a hydrophilic side and a hydrophobic side. The absorbent member may be positioned between the upstream layer and the downstream layer. The hydrophilic side of the upstream layer may be positioned adjacent to and facing the absorbent member so that the hydrophobic side of the upstream layer may form a portion of an exterior of the apparatus. The hydrophilic side of the downstream layer may be positioned adjacent to and facing the absorbent member so that the hydrophobic side of the downstream layer may form another portion of the exterior of the apparatus. Fluids incident on the exterior of the apparatus may be laterally distributed along the exterior of the apparatus before being absorbed by the absorbent member.

According to yet another illustrative embodiment, an apparatus for collecting fluid from a tissue site may include an upstream layer, a sealing member, and an absorbent member. The upstream layer may have a hydrophilic side and a hydrophobic side. The sealing member may be adapted to cover the tissue site and the upstream layer, and the sealing member may be bonded to the upstream layer. The hydrophilic side of the upstream layer may be positioned to face the sealing member. The absorbent member may be positioned between the upstream layer and the sealing member.

According to still another illustrative embodiment, an apparatus for collecting fluid from a tissue site may include an upstream layer, a downstream layer, an absorbent member, a sealing member, and a non-adherent interface. The upstream layer may have a hydrophilic side and a hydrophobic side, and the downstream layer may have a hydrophilic side and a hydrophobic side. The absorbent member may be positioned between the upstream layer and the downstream layer. The hydrophilic side of the upstream layer may be positioned facing the absorbent member, and the hydrophilic side of the downstream layer may be positioned facing the absorbent member. The sealing member may be positioned adjacent to the downstream layer. The non-adherent interface may be adapted to be positioned between the upstream layer and the tissue site. The sealing member may be bonded to the downstream layer by a first hot-melt web layer, and the non-adherent interface may be bonded to the upstream layer by a second hot-melt web layer.

According to yet another illustrative embodiment, a method for treating a tissue site may include positioning a manifold adjacent to the tissue site, providing a pouch, positioning the pouch adjacent to the manifold, covering the manifold and the pouch with a sealing member, extracting fluid from the tissue site, and distributing the fluid along the exterior of the pouch. The pouch may include an upstream layer having a hydrophilic side and a hydrophobic side, a downstream layer having a hydrophilic side and a hydrophobic side, and an absorbent member enclosed between the upstream layer and the downstream layer. The hydrophilic side of the upstream layer may be positioned facing the absorbent member so that the hydrophobic side of the upstream layer may form a portion of an exterior of the pouch. The hydrophilic side of the downstream layer may be positioned facing the absorbent member. The method may include positioning the pouch adjacent to the manifold so that the hydrophobic side of the upstream layer may be adjacent to the manifold. The manifold and the pouch may be covered with a sealing member to provide a fluid seal between the sealing member and the tissue site. The method may also include extracting fluid from the tissue site and distributing the fluid laterally along the exterior of the pouch before absorbing the fluid in the absorbent member for storage.

According to another illustrative embodiment, a method for manufacturing a fluid storage apparatus may include providing a first layer having a hydrophilic side and a hydrophobic side, positioning an absorbent member adjacent to the hydrophilic side of the first layer, providing a second layer having a hydrophilic side and a hydrophobic side, and positioning the hydrophilic side of the second layer adjacent to the absorbent member. The second layer may be positioned on an opposite side of the absorbent member from the first layer. The method may also include coupling peripheral portions of the first layer and the second layer to enclose the absorbent member.

Other aspects, features, and advantages of the illustrative embodiments will become apparent with reference to the drawings and detailed description that follow.

BRIEF DESCRIPTION OF THE DRAWINGS

FIG. 2 is a sectional view of an illustrative embodiment of a pouch associated with a wound dressing depicted in the reduced-pressure therapy system of FIG. 1;

FIG. 3 is an exploded sectional view of the pouch of FIG. 2;

FIG. 4 is a sectional view depicting another illustrative embodiment of a wound dressing;

FIG. 5 is a sectional view depicting another illustrative embodiment of a wound dressing.

DETAILED DESCRIPTION OF ILLUSTRATIVE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

The exemplary embodiments may also be described herein in the context of reduced-pressure therapy applications, but many of the features and advantages are readily applicable to other environments and industries. For example, the exemplary embodiments may be used with or without reduced-pressure therapy.

Figure 1:
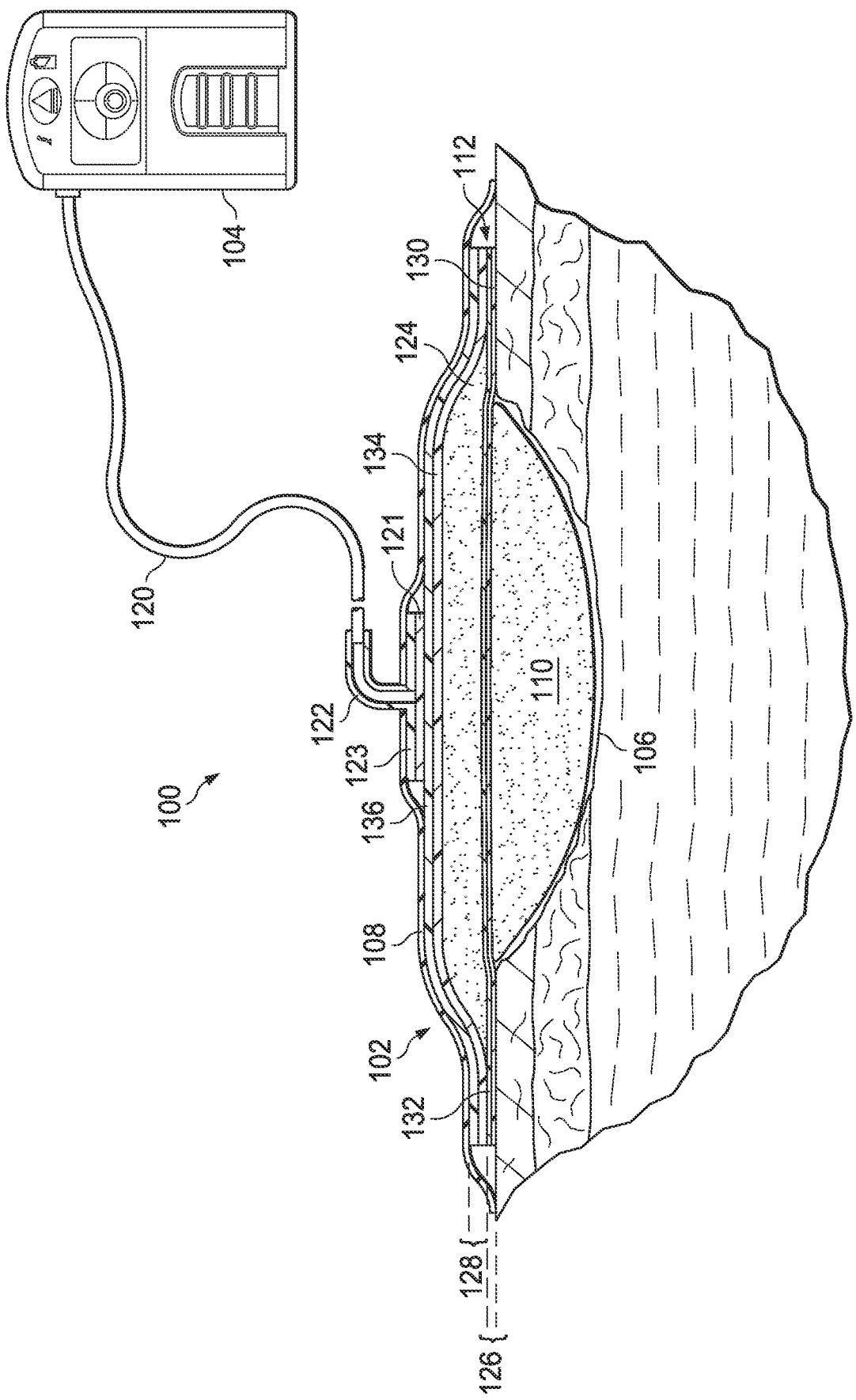
FIG. 1 is sectional view illustrating a reduced-pressure therapy system in accordance with an exemplary embodiment.

Referring to FIG. 1, a therapy system 100 may comprise a dressing 102 in fluid communication with a tissue site 106, an optional reduced-pressure source 104 for providing reduced pressure to a tube 120 fluidly coupled to the reduced-pressure source 104, and a connector 122 fluidly coupling the tube 120 to the dressing 102.

The term "tissue site" may refer to a wound or defect located on or within tissue, including without limitation, bone tissue, adipose tissue, muscle tissue, neural tissue, dermal tissue, vascular tissue, connective tissue, cartilage, tendons, or ligaments. A tissue site may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

A reduced-pressure source, such as the reduced-pressure source 104, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure may be between about −5 mm Hg (−667 Pa) and about −500 mm Hg (−66.7 kPa). In some embodiments, the pressure may be between about −75 mm Hg (−9.9 kPa) and about −300 mm Hg (−39.9 kPa).

In general, exudates and other fluids may flow toward lower pressure along a fluid path. Further, fluids may be attracted to flow through permeable materials along a path of increasing hydrophilicity or absorbency among the materials. Thus, the term "downstream" may refer to components that are further along a fluid path than components that may be referred to as "upstream."

"Reduced pressure" may refer to a pressure less than a local ambient pressure, such as the ambient pressure in a local environment external to a sealed therapeutic environment. The local ambient pressure may also be the atmospheric pressure at which a patient is located. Further, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The components of the therapy system 100 may be coupled directly or indirectly. Components may be fluidly coupled to each other to provide a path for transferring fluids (for example, liquid and/or gas) between the components. In some exemplary embodiments, components may be fluidly coupled with a conduit, such as the tube 120, for example. A "tube," as used herein, may refer to a pipe, hose, conduit, or elongated structure with one or more lumina adapted to convey fluids between two ends. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The reduced pressure developed by the reduced-pressure source 104 may be delivered through the tube 120 to the connector 122. The connector 122 may be a device configured to fluidly couple the reduced-pressure source 104 to the dressing 102. For example, reduced pressure may be provided to the dressing 102 through a port disposed in the connector 122. In some exemplary embodiments, the connector 122 may include a flange portion 123 that couples to the dressing 102 for securing the connector 122 to the dressing 102. The connector 122 may also include a primary filter 121 positioned in fluid communication between the dressing 102 and the connector 122. The primary filter 121 may comprise a hydrophobic material adapted to limit passage of liquids through the connector 122 into the tube 120. In one exemplary embodiment, the connector 122 may be a T.R.A.C.® Pad or Sensa T.R.A.C.® Pad available from Kinetic Concepts, Inc. of San Antonio, Tex. In other exemplary embodiments, the connector 122 may also be a conduit inserted into the dressing 102.

The dressing 102 may include an optional manifold 110 adapted to be in fluid communication with the tissue site 106, a pouch 112 adapted to be in fluid communication between the tissue site 106 or the manifold 110 and the connector 122, and a drape 108 covering the optional manifold 110 and the pouch 112 at the tissue site 106. The manifold 110 may be placed within, over, on, or otherwise proximate to the tissue site 106. The pouch 112 may be placed adjacent the manifold 110, and the drape 108 may be placed over the manifold 110 and sealed to tissue proximate to the tissue site 106. The tissue proximate to the tissue site 106 may be undamaged epidermis peripheral to the tissue site 106. Thus, the dressing 102 can provide the sealed therapeutic environment proximate to the tissue site 106, substantially isolating the tissue site 106 from the external environment. The reduced-pressure source 104 can reduce the pressure in the sealed therapeutic environment. Reduced pressure applied uniformly through the manifold 110 in the sealed therapeutic environment can induce macrostrain and microstrain in the tissue site 106, as well as remove exudates and other fluids from the tissue site 106, which can be collected in the pouch 112 and disposed of properly.

In the exemplary embodiment illustrated in FIG. 1, the manifold 110 may contact the tissue site 106. The manifold 110 may be partially or fully in contact with the tissue site 106. If the tissue site 106 extends into tissue from a tissue surface, for example, the manifold 110 may partially or completely fill the tissue site 106. In other exemplary embodiments, the manifold 110 may be placed over the tissue site 106. The manifold 110 may take many forms, and may have many sizes, shapes, or thicknesses depending on a variety of factors, such as the type of treatment being implemented or the nature and size of the tissue site 106. For example, the size and shape of the manifold 110 may be adapted to the contours of deep and irregular shaped tissue sites.

The manifold 110 may comprise a substance or structure adapted to distribute reduced pressure to a tissue site, remove fluids from a tissue site, or distribute reduced pressure to and remove fluids from a tissue site. In some exemplary embodiments, the manifold 110 may also facilitate delivering fluids to a tissue site, for example, if the fluid path is reversed or a secondary fluid path is provided. The manifold 110 may include flow channels or pathways that distribute fluids provided to and removed from a tissue site around the manifold 110. In one exemplary embodiment, the flow channels or pathways may be interconnected to improve distribution of fluids provided to or removed from a tissue site. For example, cellular foam, open-cell foam, porous tissue collections, and other porous material, such as gauze or felted mat may include structural elements arranged to form flow channels. Liquids, gels, and other foams may also include or be cured to include flow channels.

In one exemplary embodiment, the manifold 110 may be a porous foam material having interconnected cells or pores adapted to distribute reduced pressure to the tissue site 106 in a substantially uniform manner. The foam material may be either hydrophobic or hydrophilic. In one non-limiting example, the manifold 110 can be an open-cell, reticulated polyurethane foam such as GranuFoam® dressing available from Kinetic Concepts, Inc. of San Antonio, Tex.

In an example in which the manifold 110 may be made from a hydrophilic material, the manifold 110 may also wick fluid away from the tissue site 106, while continuing to distribute reduced pressure to the tissue site 106. The wicking properties of the manifold 110 may draw fluid away from the tissue site 106 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 110 may further promote granulation at the tissue site 106 when pressure within the sealed therapeutic environment is reduced. For example, any or all of the surfaces of the manifold 110 may have an uneven, coarse, or jagged profile that can induce microstrains and stresses at the tissue site 106 when reduced pressure is applied through the manifold 110 to the tissue site 106.

In one exemplary embodiment, the manifold 110 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and caprolactones. The manifold 110 may further serve as a scaffold for new cell-growth, or a scaffold material may be used in conjunction with the manifold 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 or sealing member may be constructed from a material that can provide a fluid seal between two components or two environments, such as between the sealed therapeutic environment and a local ambient environment. The drape 108 may be, for example, an impermeable or semi-permeable, elastomeric material that can provide a seal adequate to maintain a reduced pressure at a tissue site for a given reduced-pressure source. For semi-permeable materials, the permeability generally should be low enough that a desired reduced pressure may be maintained, while permitting moisture vapor to pass through. The drape 108 may further include an attachment device that may be used to attach the drape 108 to an attachment surface, such as undamaged epidermis, a gasket, or another sealing member. The attachment device may take many forms. For example, an attachment device may be a medically acceptable, pressure-sensitive adhesive that extends about a periphery, a portion of, or an entirety of the drape 108. Other exemplary embodiments of an attachment device may include a double-sided tape, paste, hydrocolloid, hydrogel, silicone gel, organogel, or an acrylic adhesive.

Referring to FIG. 2, the pouch 112 may include an absorbent member 124, a first outer layer, such as an upstream layer 126, and a second outer layer, such as a downstream layer 128. The upstream layer 126 and the downstream layer 128 envelop or enclose the absorbent member 124. The absorbent member 124 may absorb fluids transmitted through the upstream layer 126, for example.

The absorbent member 124 may be formed of or include an absorbent material. The absorbent material may hold, stabilize, and/or solidify fluids that may be collected from the tissue site 106. The absorbent material may be of the type referred to as "hydrogels," "super-absorbents," or "hydrocolloids." The absorbent material may include fibers or spheres capable of manifolding reduced pressure. Spaces or voids between the fibers or spheres may allow a reduced pressure that is supplied to the dressing 102 to be transferred within and through the absorbent member 124 to the manifold 110 and the tissue site 106. In some exemplary embodiments, the absorbent material may be Texsus FP2325 having a material density of 800 grams per square meter (gsm), or Texsus CCBSL130LL. In other exemplary embodiments, the absorbent material may be BASF Luquafleece 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the upstream layer 126 and the downstream layer 128 have perimeter dimensions that are larger than the perimeter dimensions of the absorbent member 124 so that, when the absorbent member 124 is positioned between the upstream layer 126 and the downstream layer 128, the upstream layer 126 and the downstream layer 128 extend beyond the perimeter of the absorbent member 124. In some exemplary embodiments, the upstream layer 126 and the downstream layer 128 surround the absorbent member 124. Peripheral portions of the upstream layer 126 and the downstream layer 128 may be coupled so that the upstream layer 126 and the downstream layer 128 enclose the absorbent member 124. The upstream layer 126 and the downstream layer 128 may be coupled by high frequency welding, ultrasonic welding, heat welding, or impulse welding, for example. In other exemplary embodiments, the upstream layer 126 and the downstream layer 128 may be coupled by bonding or folding, for example.

Referring to FIGS. 2 and 3, the upstream layer 126 may comprise a first side such as a hydrophobic side 130, and a second side such as a hydrophilic side 132. The hydrophilic side 132 may be positioned adjacent to and facing the absorbent member 124. The hydrophobic side 130 may be positioned facing the tissue site 106. In this manner, the hydrophobic side 130 of the upstream layer 126 may be an upstream side of the pouch 112. The upstream layer 126 may be formed of non-woven material having a thickness 138. In some exemplary embodiments, the upstream layer 126 may have a polyester fibrous porous structure. The upstream layer 126 may not be perforated. In some embodiments, the upstream layer 126 may be formed of Libeltex TDL2 or Libeltex TL4, and may have a material density between about 80 gsm to about 150 gsm. In other exemplary embodiments, the material density may be lower or greater depending on the particular application of the pouch 112. Further, in some embodiments, multiple layers of material may be used to achieve a desired thickness for the upstream layer 126.

The hydrophobic side 130 may be configured to distribute fluids along the upstream side of the pouch 112. The hydrophobic side 130 may also be referred to as a wicking side, wicking surface, distribution surface, distribution side, or fluid distribution surface. The hydrophobic side 130 may be a smooth distribution surface configured to move fluid through the upstream layer 126 along a grain of the upstream layer 126, distributing fluid throughout the upstream layer 126. The hydrophilic side 132 may be configured to acquire fluid from the hydrophobic side 130 to aid in fluid movement into the absorbent member 124. The hydrophilic side 132 may also be referred to as a fluid acquisition surface, fluid acquisition side, hydrophilic acquisition surface, or hydrophilic acquisition side. The hydrophilic side 132 may be a fibrous surface and be configured to draw fluid into the upstream layer 126. While illustrated in FIG. 3 as separate components, the hydrophilic side 132 and the hydrophobic side 130 of the upstream layer 126 are opposite sides of the upstream layer 126 and are shown as separate components to aid in explanation of the described exemplary embodiments.

The downstream layer 128 may comprise a first side such as a hydrophilic side 134, that may be adjacent to and facing the absorbent member 124, and a second side such as a hydrophobic side 136. The hydrophobic side 136 of the downstream layer 128 may also be a downstream side of the pouch 112. The downstream layer 128 may be formed of a non-woven material having a thickness 140. In some exemplary embodiments, the downstream layer 128 may have a polyester fibrous porous structure. The downstream layer 128 may not be perforated. In some embodiments, the downstream layer 128 may be formed of Libeltex TDL2 or Libeltex TL4, and may have a material density between about 80 gsm to about 150 gsm. In other exemplary embodiments, the material density may be lower or greater depending on the particular application of the pouch 112. The material density of the downstream layer 128 may be greater than the material density of the upstream layer 126. Further, in some embodiments, multiple layers of material may be used to achieve a desired thickness for the downstream layer 128. In some embodiments, the thickness 140 of the downstream layer 128 may be greater than the thickness 138 of the upstream layer 126. In the exemplary embodiment illustrated in FIGS. 2 and 3, for example, the thickness 140 may be about three times greater than the thickness 138.

In some embodiments, the upstream layer 126 and/or the downstream layer 128 may be partially formed of an anti-microbial material. In such example embodiments, the upstream layer 126 and/or downstream layer 128 may include a polyhexanide or polyhexamethylene biguanide (PHMB) anti-microbial within the structure to provide for longer dressing life. Other materials may be incorporated with the upstream layer 126 and/or downstream layer 128. For example, Collagen or Collagen ORC (oxidized regenerated cellulose) may be bonded to either the upstream layer 126 or the downstream layer 128 to modulate matrix metalloproteinases (MMPs) at the tissue site 106. Collagen ORC has been shown to improve re-epithelialization time in chronic wounds.

The hydrophilic side 134 of the downstream layer 128 may be disposed adjacent to and facing the absorbent member 124 on an opposite side of the absorbent member 124 from the hydrophilic side 132 of the upstream layer 126. The hydrophilic side 134 of the downstream layer 128 may be configured to acquire excess fluids not absorbed by the absorbent member 124. The hydrophilic side 134 of the downstream layer 128 may also be referred to as a fluid acquisition surface, fluid acquisition side, hydrophilic acquisition surface, or hydrophilic acquisition side. The hydrophilic side 134 of the downstream layer 128 may be a fibrous surface and be configured to draw fluid into the downstream layer 128. The hydrophobic side 136 of the downstream layer 128 may be configured to distribute fluids not contained by the absorbent member 124 and the hydrophilic side 134 of the downstream layer 128. The hydrophobic side 136 may also be referred to as a wicking side, wicking surface, distribution surface, distribution side, or fluid distribution surface. The hydrophobic side 136 may be a smooth distribution surface configured to move fluid through the downstream layer 128 along a grain of the downstream layer 128, distributing fluid throughout the downstream layer 128. While illustrated in FIG. 3 as separate components, the hydrophilic side 134 and the hydrophobic side 136 are opposite sides of the downstream layer 128 and are shown as separate components to aid in explanation of the described exemplary embodiments.

When fluid is being absorbed, some absorbent materials may become saturated at the point of fluid entry into the absorbent member itself. When the absorbent material becomes saturated in one area prior to saturation of the absorbent material in other areas, the absorbent material may experience a reduced ability to move fluid from the point of entry to areas of the absorbent material that are unsaturated. In addition, if reduced pressure is being applied, the amount of reduced pressure distributed to the tissue site may be reduced, decreasing the therapeutic benefits of using reduced pressure. When absorbency and fluid management is reduced as described above, more frequent dressing changes are needed, thereby increasing cost.

As disclosed herein, the therapy system 100 may overcome these shortcomings and others. For example, by placing the hydrophobic side 130 of the upstream layer 126 facing the tissue site 106 adjacent to the manifold 110, the hydrophobic nature of the hydrophobic side 130 may move fluid along a grain (not shown) of the hydrophobic side 130 laterally along a width of the upstream layer 126. In this manner, the fluid may move parallel to the manifold 110 and the tissue site 106. The lateral movement of the fluid may be substantially normal relative to a vertical or downstream movement of the fluid away from the tissue site 106 toward the drape 108. This wicking action may spread the fluid drawn from the tissue site 106 laterally across a wider area before the fluid enters the hydrophilic side 132 and the absorbent member 124. As the fluid moves through the upstream layer 126 from the hydrophobic side 130 toward the absorbent member 124, the hydrophilic side 132 becomes wetted with the fluid, permitting the fluid to be drawn into the absorbent member 124. The gradient of hydrophilicity or absorbency increases from the hydrophobic side 130 to the hydrophilic side 132, and thus, the fluid moves downstream away from the tissue site 106 and toward the absorbent member 124. The application of reduced pressure to the dressing 102 may further enhance the downstream movement of the fluid.

In operation, the increased thickness 140 and increased material density of the downstream layer 128 may aid the distribution of reduced pressure to the upstream layer 126 and the manifold 110. In one exemplary embodiment, the upstream layer 126 may have a density of about 80 gsm, and the downstream layer 128 may have a density of about 150 gsm so that the relative thickness of the downstream layer 128 to the upstream layer 126 is about 1.875. The relative thickness of the downstream layer 128 to the upstream layer 126 in other exemplary embodiments may fall in the range from about 1.5 to about 3.0 for other applications. The distribution of reduced pressure by the downstream layer 128 may aid the wicking action of the hydrophobic side 130 of the upstream layer 126 so that fluids drawn from the tissue site 106 may be more evenly distributed in the dressing 102. In turn, more even distribution of the fluids drawn from the tissue site 106 may provide for more efficient use of the absorbent member 124, increasing the time between replacement of the dressing 102, and decreasing costs as fewer dressings are needed to absorb an equivalent amount of fluid.

By configuring the downstream layer 128 with the hydrophobic side 136 on the top side of the pouch 112, the dressing 102 may acquire free fluids from the absorbent member 124 when the absorbent member 124 becomes saturated, or gel-blocked, in one region. The dressing 102 may then wick and redistribute fluids over the top of the dressing 102 such that fluid wicking is occurring on both sides of the pouch 112. For example, when a region of the absorbent material 124 becomes saturated, the hydrophilic side 134 of the downstream layer 128 may draw and acquire excess fluid from the absorbent material 124 into an adjacent portion of the hydrophilic side 134. This excess fluid may then migrate into the hydrophobic side 136 of the downstream layer 128. The hydrophobic nature of the hydrophobic side 136 may move the fluid along a grain (not shown) of the hydrophobic side 136 laterally along a width of the downstream layer 128. When the fluid reaches a location where the underlying hydrophilic side 134 of the downstream layer 128 and the absorbent member 124 are not saturated, the fluid may be drawn back down from the outer surface of the hydrophobic side 136 into the hydrophilic side 134 and the absorbent member 124. Because of the increasing gradient of hydrophilicity from the hydrophobic side 136 to the hydrophilic side 134 and further to the absorbent member 124, the fluid will be drawn back upstream toward the absorbent member 124, now into a region of the absorbent member 124 that is not saturated. This provides optimal fluid distribution and absorption in the pouch 112, and furthermore may prevent premature saturation or gel-blocking of the absorbent material 124.

Positioning of the upstream layer 126 and the downstream layer 128, as described herein, may orient grains of the upstream layer 126 and the downstream layer 128 in a manner that increases the efficient use of the absorbent member 124. By using materials that provide a wicking function, the efficient use of available absorbent materials can be improved.

The use of layers that wick fluids and manifold reduced pressure allows for controlled use of the available absorbent material. The layers, arranged as described above, distribute reduced pressure such that fluid may be more evenly distributed to the absorbent member of the pouch, increasing the total time necessary to saturate the absorbent materials of the absorbent member as more fluid pathways are used to distribute the fluid. The use of layers to form the pouch with structures of differing hydrophilicity allows for better control of the fluids entering the absorbent member of the pouch. The use of layers having different coatweights allows the properties of the pouch to be matched to the application in a technically better and cost effective solution. The solution disclosed will result in a greater level of absorption before capacity is reached without requiring additional absorbent material.

Referring to FIG. 4, depicted is another illustrative embodiment of a dressing 400 suitable for use with the therapy system 100. The dressing 400 may comprise the upstream layer 126, the absorbent member 124, and the drape 108. Similar to the embodiments of FIGS. 2-3, the upstream layer 126 may comprise the hydrophobic side 130 and the hydrophilic side 132. The hydrophilic side 132 may be positioned adjacent to and facing the absorbent member 124 such that the hydrophobic side 130 of the upstream layer 126 is also an upstream side of the dressing 400. In this manner, the hydrophobic side 130 may be adapted to be positioned facing the tissue site 106 and the manifold 110 as shown in FIG. 1. Analogous to the embodiments of FIGS. 1-3, the hydrophobic side 130 may be configured to distribute fluids along the upstream layer 126, while the hydrophilic side 132 may be configured to acquire fluid from the hydrophobic side 130 and assist with moving the fluid into the absorbent member 124. The upstream layer 126 may be formed of non-woven material having a thickness 138. In some exemplary embodiments, the upstream layer 126 may have a polyester fibrous porous structure. The upstream layer 126 may not be perforated. In some embodiments, the upstream layer 126 may be formed of Libeltex TDL2 or Libeltex TL4, and may have a material density between about 80 gsm to about 150 gsm. In other exemplary embodiments, the material density may be lower or greater depending on the particular application of the pouch 112.

Continuing with FIG. 4, the drape 108 of the dressing 400 may cover both the upstream layer 126 and the absorbent member 124. The drape 108 may be placed adjacent to the absorbent member 124 and extend beyond the edges of the absorbent member 124 to attach to the upstream layer 126. The drape 108 may further include an attachment device that may be used to attach the drape 108 to the surface of the upstream layer 126. In this manner, the absorbent member 124 may be enclosed within or surrounded by the drape 108 and the upstream layer 126 of the dressing 400.

Referring to FIG. 5, depicted is another illustrative embodiment of a dressing 500 suitable for use with the therapy system 100. Similar to the embodiments depicted in FIGS. 2-3, the dressing 500 may comprise the pouch 112 and the drape 108. The pouch 112 may comprise an upstream layer 126, an absorbent member 124, and a downstream layer 128. As described for FIGS. 2-3, the upstream layer 126 of the pouch 112 may comprise the hydrophobic side 130 and the hydrophilic side 132. The hydrophilic side 132 may be positioned adjacent to and facing the absorbent member 124. The hydrophobic side 130 may be adapted to face the tissue site 106 and the manifold 110. The hydrophobic side 130 may be configured to distribute fluids along the upstream layer 126, while the hydrophilic side 132 may be configured to acquire fluid from the hydrophobic side 130 and assist with moving the fluid into the absorbent member 124.

The downstream layer 128 of the pouch 112 may comprise the hydrophilic side 134 adjacent to and facing the absorbent member 124. As described above, the hydrophobic side 136 of the downstream layer 128 may be the downstream side of the pouch 112. The hydrophilic side 134 of the downstream layer 128 may be disposed adjacent to the absorbent member 124 on the opposite side of the absorbent member 124 from the hydrophilic side 132 of the upstream layer 126. Analogous to the previous embodiments, the hydrophilic side 134 may be configured to acquire fluids not contained by the absorbent member 124 for distribution by the hydrophobic side 136 of the downstream layer 128. The hydrophobic side 136 may be configured to laterally move fluid along a grain of the downstream layer 128 for absorption by the absorbent member 124.

Still referring to FIG. 5, the dressing 500 may additionally include an optional non-adherent layer 502. The non-adherent layer 502 may be positioned adjacent to the hydrophobic side 130 of the upstream layer 126. The non-adherent layer 502 may be placed between the hydrophobic side 130 of the upstream layer 126 and the tissue site 106, and may be adapted to prevent adherence of the tissue site 106 to the upstream layer 126. The non-adherent layer 502 may also function to hold the dressing 500 in place against the tissue site 106. The non-adherent layer 502 may be a perforated silicone sheet or a pattern-coated silicone sheet with registered "dots" of acrylic adhesive. For example, perforations 504 may provide fluid communication between the tissue site 106 and the pouch 112. The acrylic adhesive may prevent the dressing 500 from moving under shear stresses, such as those associated with a sacral wound.

In another illustrative embodiment (not shown), the components of the dressing according to this disclosure may be configured as a borderless, laminated structure. For example, referring to the embodiments of FIGS. 1-3, the adjacent surfaces of the drape 108, the downstream layer 128, the absorbent member 124, and the upstream layer 126 may be laminated or coupled together. A heat melted polyester material or other bonding agent, for example, may be positioned between the adjacent surfaces of these components for coupling the components together as a laminate structure. Coupling the adjacent surfaces of the dressing components to one another may provide a borderless structure having exposed edges. In this manner, peripheral portions of the components may not be coupled to one another, permitting each of the components to have exposed edges. In some embodiments, a hydrophilic foam interface may be included in the laminate for positioning adjacent the tissue site as a non-adherent interface.

Figure 6:
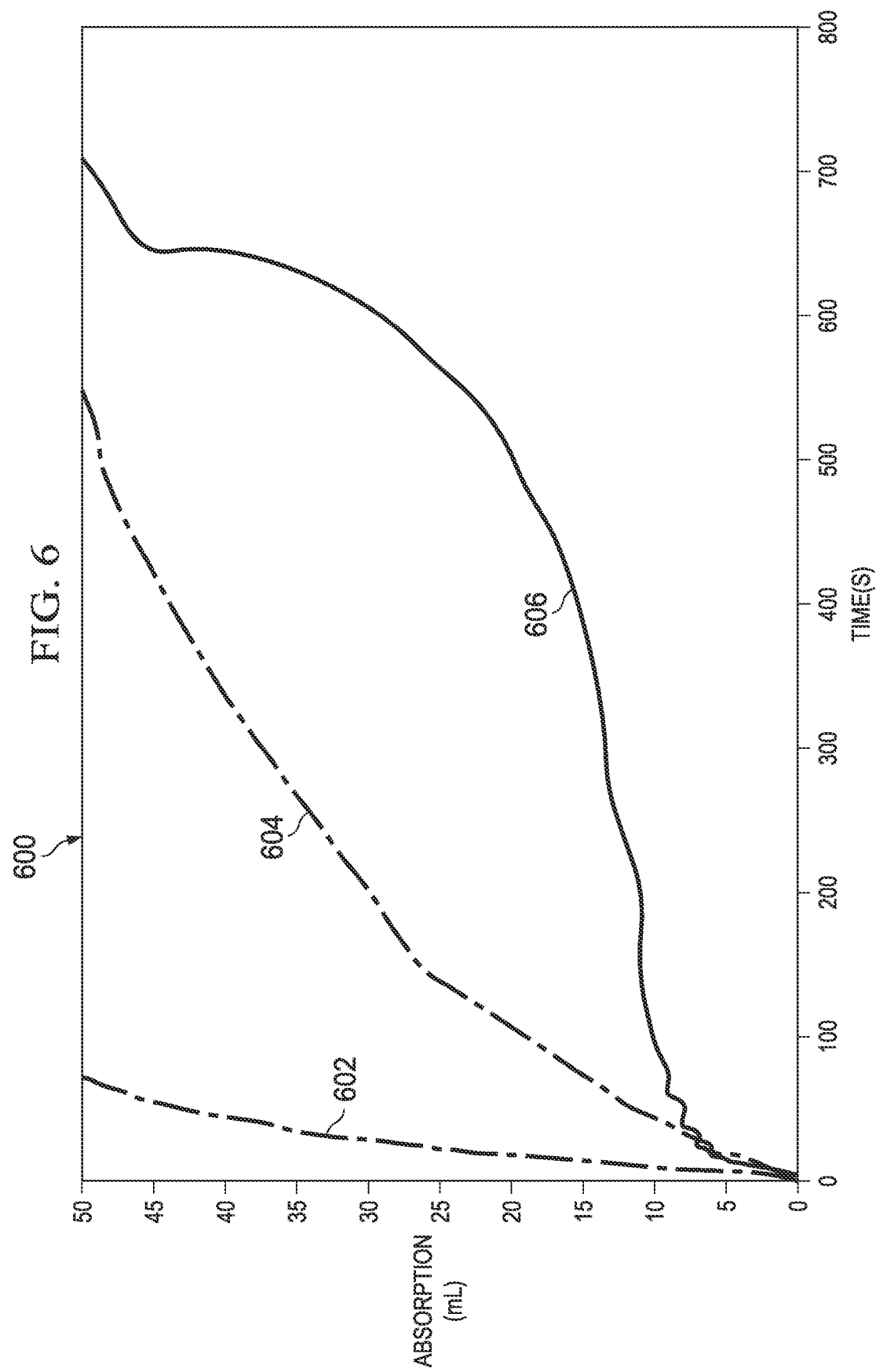
FIG. 6 is a graph showing improved absorption capabilities associated with a wound dressing according to this disclosure.

FIG. 6 shows improved absorption and wicking capabilities associated with a dressing according to this disclosure. The absorption comparison plot 600 compares the time for 50 ml of saline solution to be delivered and absorbed by and among a dressing according to this disclosure identified by plot 602 and prior art dressings identified by plots 604 and 606. The absorption comparison plot 600 shows the dressing of plot 602 performing better at acquiring and absorbing a 0.9% saline solution at 4 inches of fluid head than the prior art dressings of plots 604 and 606.

The systems and methods described herein may provide significant advantages, some of which have already been mentioned. For example, the therapy system may provide improved efficiency, lower cost, and enhanced manifolding of reduced pressure. The disclosed exemplary embodiments may also be used with inline canisters, for example, fluid absorbing pouches or fluid absorbing canisters disposed external to the dressing.

Although certain illustrative, non-limiting exemplary embodiments have been presented, various changes, substitutions, permutations, and alterations can be made without departing from the scope of the appended claims. Any feature described in connection to any one exemplary embodiment may also be applicable to any other exemplary embodiment. Further, the steps of the methods described herein may be carried out in any suitable order, or simultaneously where appropriate.

We claim:

1. An apparatus for collecting fluid from a tissue site, comprising:
    an upstream layer having a hydrophilic side and a hydrophobic side;
    a downstream layer having a hydrophilic side and a hydrophobic side; and
    an absorbent member positioned between the upstream layer and the downstream layer, the hydrophilic side of the upstream layer positioned adjacent to and facing the absorbent member so that the hydrophobic side of the upstream layer forms a portion of an exterior of the apparatus, and the hydrophilic side of the downstream layer positioned adjacent to and facing the absorbent member so that the hydrophobic side of the downstream layer forms another portion of the exterior of the apparatus;
    wherein the exterior of the apparatus is adapted to laterally distribute fluids along the exterior before the fluids are absorbed by the absorbent member.

2. The apparatus of claim 1, wherein the upstream layer has a first thickness and the downstream layer has a second thickness, the second thickness being greater than the first thickness.

3. The apparatus of claim 1, wherein the upstream layer has a material density of about 80 gsm.

4. The apparatus of claim 1, wherein the upstream layer and the downstream layer each comprise a peripheral portion extending beyond the absorbent member, the peripheral portion of the upstream layer being coupled to the peripheral portion of the downstream layer and encapsulating the absorbent member.

5. The apparatus of claim 1, wherein the downstream layer has a material density of about 150 gsm.

6. The apparatus of claim 1, wherein the upstream layer is adapted to be positioned adjacent the tissue site.

7. The apparatus of claim 1, wherein the upstream layer and the downstream layer comprise an anti-microbial material.

8. The apparatus of claim 7, wherein the anti-microbial material comprises polyhexanide or polyhexamethylene biguanide (PHMB).

9. The apparatus of claim 1, further comprising a sealing member coupled to the downstream layer.

10. The apparatus of claim 1, further comprising collagen or collagen oxidized regenerated cellulose (ORC) bonded to the upstream layer.

11. The apparatus of claim 1, further comprising a sealing member coupled to the upstream layer.

12. An apparatus for collecting fluid from a tissue site, comprising:
    an upstream layer having a hydrophilic side and a hydrophobic side;
    a downstream layer having a hydrophilic side and a hydrophobic side, the downstream layer having a material density of about 150 gsm; and
    an absorbent member positioned between the upstream layer and the downstream layer, the hydrophilic side of the upstream layer positioned adjacent to and facing the absorbent member so that the hydrophobic side of the upstream layer forms a portion of an exterior of the apparatus, and the hydrophilic side of the downstream layer positioned adjacent to and facing the absorbent member so that the hydrophobic side of the downstream layer forms another portion of the exterior of the apparatus;
    wherein the exterior of the apparatus is adapted to laterally distribute fluids along the exterior before the fluids are absorbed by the absorbent member.

13. The apparatus of claim 12, wherein the upstream layer has a material density of about 80 gsm.

14. An apparatus for collecting fluid from a tissue site, comprising:
    an upstream layer having a hydrophilic side and a hydrophobic side, the upstream layer having a material density of about 80 gsm;
    a downstream layer having a hydrophilic side and a hydrophobic side, the downstream layer having a material density of about 150 gsm; and
    an absorbent member positioned between the upstream layer and the downstream layer, the hydrophilic side of the upstream layer positioned adjacent to and facing the absorbent member so that the hydrophobic side of the upstream layer forms a portion of an exterior of the apparatus, and the hydrophilic side of the downstream layer positioned adjacent to and facing the absorbent member so that the hydrophobic side of the downstream layer forms another portion of the exterior of the apparatus;
    wherein the exterior of the apparatus is adapted to laterally distribute fluids along the exterior before the fluids are absorbed by the absorbent member.

* * * * *